(12) United States Patent
White et al.

(10) Patent No.: US 10,092,440 B2
(45) Date of Patent: Oct. 9, 2018

(54) COMPRESSION BELTS FOR SELECTIVE CHEST COMPRESSION FOLLOWING THORACIC AND CARDIOTHORACIC SURGERY AND FOR SELECTIVE ABDOMINAL COMPRESSION FOLLOWING ABDOMINAL SURGERY

(71) Applicant: PELVICBINDER, INC., Dallas, TX (US)

(72) Inventors: Leslie D. White, Dallas, TX (US); Michael W. Freitas, Colleyville, TX (US)

(73) Assignee: PelvicBinder, Inc., Dallas, TX (US)

( * ) Notice: Subject to any disclaimer, the term of this patent is extended or adjusted under 35 U.S.C. 154(b) by 436 days.

(21) Appl. No.: 14/987,544

(22) Filed: Jan. 4, 2016

(65) Prior Publication Data
US 2016/0310310 A1 Oct. 27, 2016

Related U.S. Application Data

(60) Provisional application No. 62/152,586, filed on Apr. 24, 2015.

(51) Int. Cl.
*A61F 5/02* (2006.01)
(52) U.S. Cl.
CPC ..................... *A61F 5/02* (2013.01)

(58) Field of Classification Search
CPC .. A61F 5/02; A61F 5/022; A61F 5/024; A61F 5/026; A61F 5/028; A61F 5/37; A61F 5/05808
See application file for complete search history.

(56) References Cited

U.S. PATENT DOCUMENTS

| | | |
|---|---|---|
| 5,226,874 A | 7/1993 | Heinz et al. |
| 5,346,461 A | 9/1994 | Heinz et al. |
| RE35,940 E | 10/1998 | Heinz et al. |
| 6,602,214 B2 | 8/2003 | Heinz et al. |
| 7,727,172 B2 * | 6/2010 | Wang ............... A61F 5/028 602/19 |
| 8,372,023 B2 * | 2/2013 | Garth ............... A61F 5/028 128/876 |

* cited by examiner

*Primary Examiner* — Tarla R Patel (57) ABSTRACT

A compression belt encircles a selected portion of a patient's body and provides temporary compression of the selected portion. The compression belt comprises an elongated belt having first and second free ends free, a tensioning cord, a handle attached to the end of the tensioning cord, closing mechanism providing a mechanical advantage, a one-way tension mechanism and a selective release mechanism. Pulling the handle causes the closing mechanism to pull the first and second free ends closer together so as to compress the selected portion of the patient's body, the one-way tension mechanism maintains compression of the patient's body, even in the absence of continued pulling of the handle, unless the selective release mechanism is activated, and activating the selected release mechanism releases the compression of the patient's body.

7 Claims, 8 Drawing Sheets

COMPRESSION BELTS FOR SELECTIVE CHEST COMPRESSION FOLLOWING THORACIC AND CARDIOTHORACIC SURGERY AND FOR SELECTIVE ABDOMINAL COMPRESSION FOLLOWING ABDOMINAL SURGERY

CROSS-REFERENCE TO RELATED APPLICATIONS

This application claims benefit of U.S. Provisional Application No. 62/152,586, filed Apr. 24, 2015, the specification of which is hereby incorporated by reference in its entirety.

TECHNICAL FIELD

The following disclosure relates to medical compression belts which may be used in post-surgical treatment of patients following, e.g., thoracic, cardiothoracic and abdominal surgeries, for stabilization of rib fractures, or for emergency stabilization of pelvic fractures. More particularly, it relates to medical compression belts fitted around a selected portion of a patient's torso, which belts can be selectively activated by the patient or technician for the temporary compression of the selected body portion and selective released by the patent or technician to end the compression.

BACKGROUND

The cardiac pillow, also known as the "heart pillow" or "cough pillow," is a therapeutic tool utilized by doctors, nurses and patients after heart surgery or other types of thoracic surgery. The cardiac pillow is a small conventional pillow often, but not always, configured in the shape of a "valentine" style heart and given to patients shortly after their heart surgery or thoracic surgery. Typically, the patent is told to temporarily press or clutch the cardiac pillow against the chest area (i.e., using the patient's own arms and hands) when sitting up, coughing, standing up or engaging in other activities that may cause discomfort to the surgery area. Used in this manner, the cardiac pillow splints the fracture in the sternum when the patient moves or breathes to lessen the patient's pain or discomfort.

There are drawbacks to the use of cardiac pillows for some patients. The cardiac pillow may become misplaced on the bed or even fall off the bed, preventing the patient from reaching it in time when needed. Some patients may not have sufficient arm or hand strength to press the pillow against the chest effectively. Further, when patients become mobile, e.g., using a walker, they do not have free hands to carry and/or use the cardiac pillow, because they must use both hands to grip the walker for safety. A need therefore exists, for a therapeutic device that can provide temporary chest compression to post-surgical thoracic patients while addressing some of the drawbacks encountered with the cardiac pillow.

Patients recovering from abdominal surgery may face medical issues similar, though not identical, to post-thoracic/cardiothoracic patents. Besides pain or discomfort caused by when sitting up, coughing, standing up, etc., abdominal patients may face the further risk of rupturing their sutures or incisions. This is especially true for obese patients. In such cases, temporary cardiac pillow type therapies may not be effective for reasons outlined above. In some cases, a conventional belt may be used to provide extra support to the abdomen; however, such belts may be uncomfortable for extended wear. A need therefore exists, for a therapeutic device that can provide temporary abdominal compression to post-surgical abdominal patients while addressing some of the drawbacks encountered with the cardiac pillow and conventional belts.

Other chest compression devices are known for the stabilization of rib fractures and pelvic compression devices are known for the emergency stabilization of pelvic fractures. Such devices often have a belt configuration with a length adjustment mechanism. However, operation of the length adjustment mechanisms of conventional devices may be complicated and/or inconvenient, making it difficult for a technician to fit the belt to the patient, and difficult to apply or release compression after the belt is fitted. A need therefore exists, for chest compression devices and pelvic compression devices that are easier to fit and operate.

SUMMARY

In one aspect thereof, a compression belt is provided for encircling a selected portion of a patient's body and providing temporary circumferential compression of the selected portion of the patient's body. The compression belt comprises an elongated belt body having a continuous length with opposing first and second free end portions and defining a centerline extending therebetween. The belt body is adapted to be wrapped circumferentially around the selected portion of the patient's body. A first pulley bank is affixed to the first end portion, the first pulley bank including at least two pulleys arranged perpendicular to the centerline of the belt body. A second pulley bank is affixed to the second end portion, the second pulley bank including at least two pulleys arranged perpendicular to the centerline of the belt body. A third pulley bank is affixed to the belt body at a fixed distance from the second pulley bank, the third pulley bank including at least two pulleys arranged perpendicular to the centerline of the belt body. A flexible cord interconnects the first, second and third pulley banks, the cord having a first cord portion extending between the pulleys of the first and second pulley banks in alternation, a second cord portion connected to the first cord portion and extending between the pulleys of the first and third pulley banks, and a third cord portion connected to the second cord portion and extending away from the third pulley bank. A handle is connected to the third cord portion, whereby withdrawing the third cord portion from the third pulley bank by pulling the handle away from the third pulley bank causes a shortening of the first cord portion such that the first and second pulley banks move closer together along with the first and second free end portions to which the respective pulley banks are affixed, thereby tightening the belt body around the selected portion of the patient's body and compressing the selected portion of the patient's body. A selectively releasable one-way cord lock mechanism is connected to the belt body, the cord lock mechanism including a frame defining a cord passage through which the third cord portion is routed after leaving the third pulley bank, a locking member mounted in the frame and movable between a locked position and a released position, the third cord portion being routed against the locking member so as to bias the locking member toward the locked position, and a release member connected to the locking member for moving the locking member between the locked position and the released position. The locking member, when in either the locked position or the released position, allows withdrawal of the third cord portion from the third pulley bank to compress the selected portion of the patient's body, when in the locked position, prevents the third cord portion from retracting into the third pulley bank to maintain compression of the selected portion of the patient's body, and when in the released position, allows the third cord portion to retract into the third pulley bank to discontinue compression of the selected portion of the patient's body.

In another aspect thereof, a compression belt encircles a selected portion of a patient's body and provides temporary compression of the selected portion. The compression belt comprises an elongated belt having first and second free ends free, a tensioning cord, a handle attached to the end of the tensioning cord, closing mechanism providing a mechanical advantage, a one-way tension mechanism and a selective release mechanism. Pulling the handle causes the closing mechanism to pull the first and second free ends closer together so as to compress the selected portion of the patient's body, the one-way tension mechanism maintains compression of the patient's body, even in the absence of continued pulling of the handle, unless the selective release mechanism is activated, and activating the selected release mechanism releases the compression of the patient's body.

BRIEF DESCRIPTION OF THE DRAWINGS

For a more complete understanding, reference is now made to the following description taken in conjunction with the accompanying Drawings in which.

DETAILED DESCRIPTION

Referring now to the drawings, wherein like reference numbers are used herein to designate like elements throughout, the various views and embodiments of compression belts for selective chest compression following thoracic and cardiothoracic surgery, for selective abdominal compression following abdominal surgery, for stabilization of rib fractures, or for emergency stabilization of pelvic fractures are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

Figure 1:
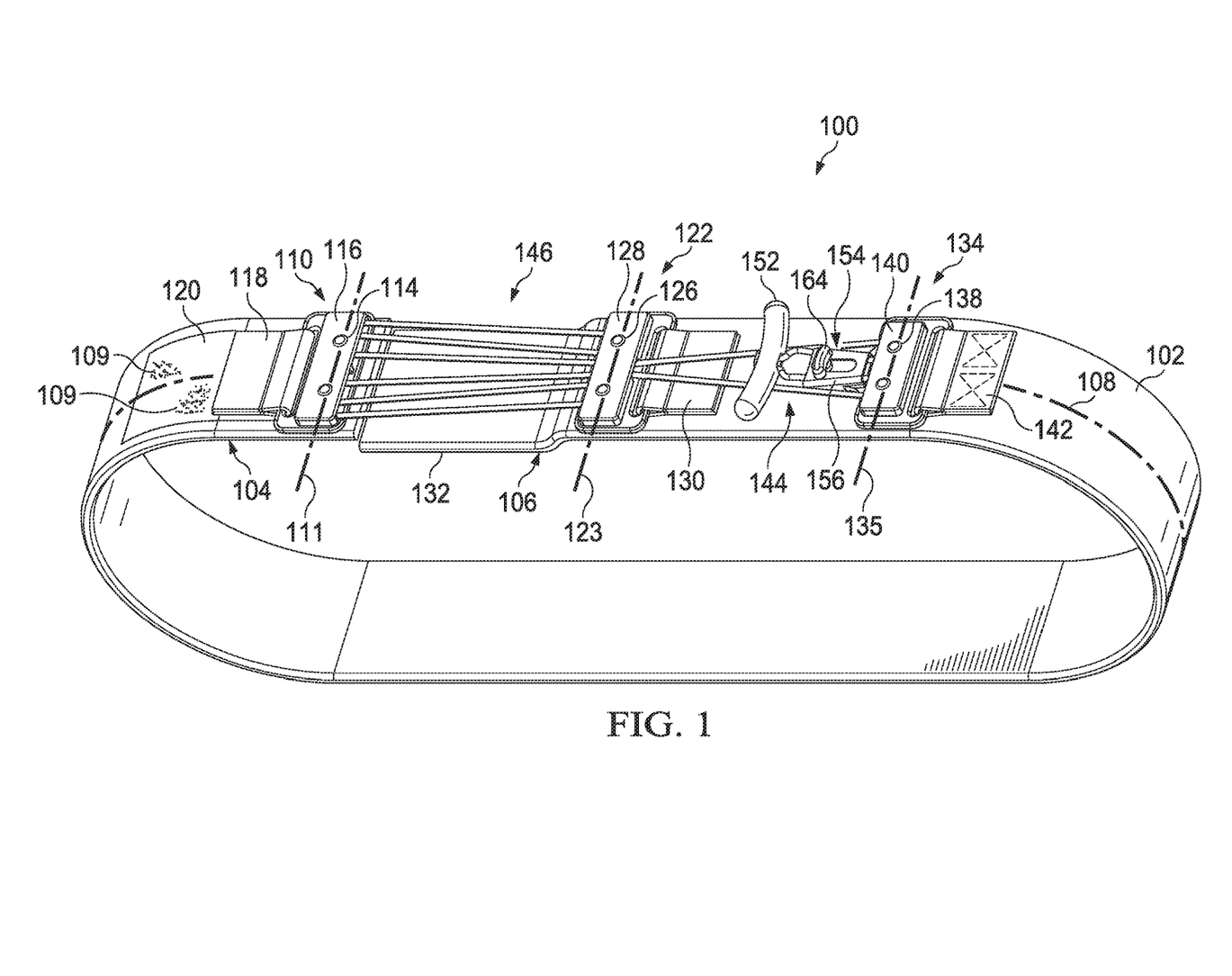
FIG. 1 shows a perspective view of a compression belt for selective temporary chest compression in accordance with one aspect.

Referring now to FIG. 1, there is illustrated a perspective view of a compression belt for selective temporary compression of a patient's chest, abdomen, pelvis or other body portion in accordance with one aspect. The compression belt 100 includes an elongated belt body 102 having a continuous length with opposing first and second free end portions 104, 106 and defining a centerline 108 extending therebetween. The belt body 102 is adapted to be wrapped circumferentially around a selected portion of the patient's body. The belt body 102 is preferably made from a fabric material that is lightweight, strong in tension, and flexible enough to be comfortable when worn for long periods of time. Selected areas of the belt body 102 may be provided with attachment material 109 to facilitate attaching or affixing other components of the belt 100 to the belt body. In particular, attachment material 109 (represented by partially patterned area) may comprise hook-and-loop type fastening material (e.g., VELCRO® brand fastening material) mounted on selected areas of the belt 100. The hook-and-loop material may comprise hook-type material, loop-type material and or both hook-and loop-type material.

In a preferred embodiment of the compression belt 100, the belt body 102 may have an overall width (measured perpendicular to the centerline 108) of about 3.0 inches and a length (measured along the centerline) of about 60 inches. If necessary, the belt body 102 may be trimmed for better fit to the patient by cutting one or both of the free end portions 104, 106. As further described below, certain elements of the compression belt 100 may be releasably affixed to the belt body 102 to facilitate trimming the belt to fit. In a preferred embodiment, the compression belt 100 will provide up to 8.0 inches of compression (this being the initial distance D2 between the first and second pulley banks described below).

Figure 2:
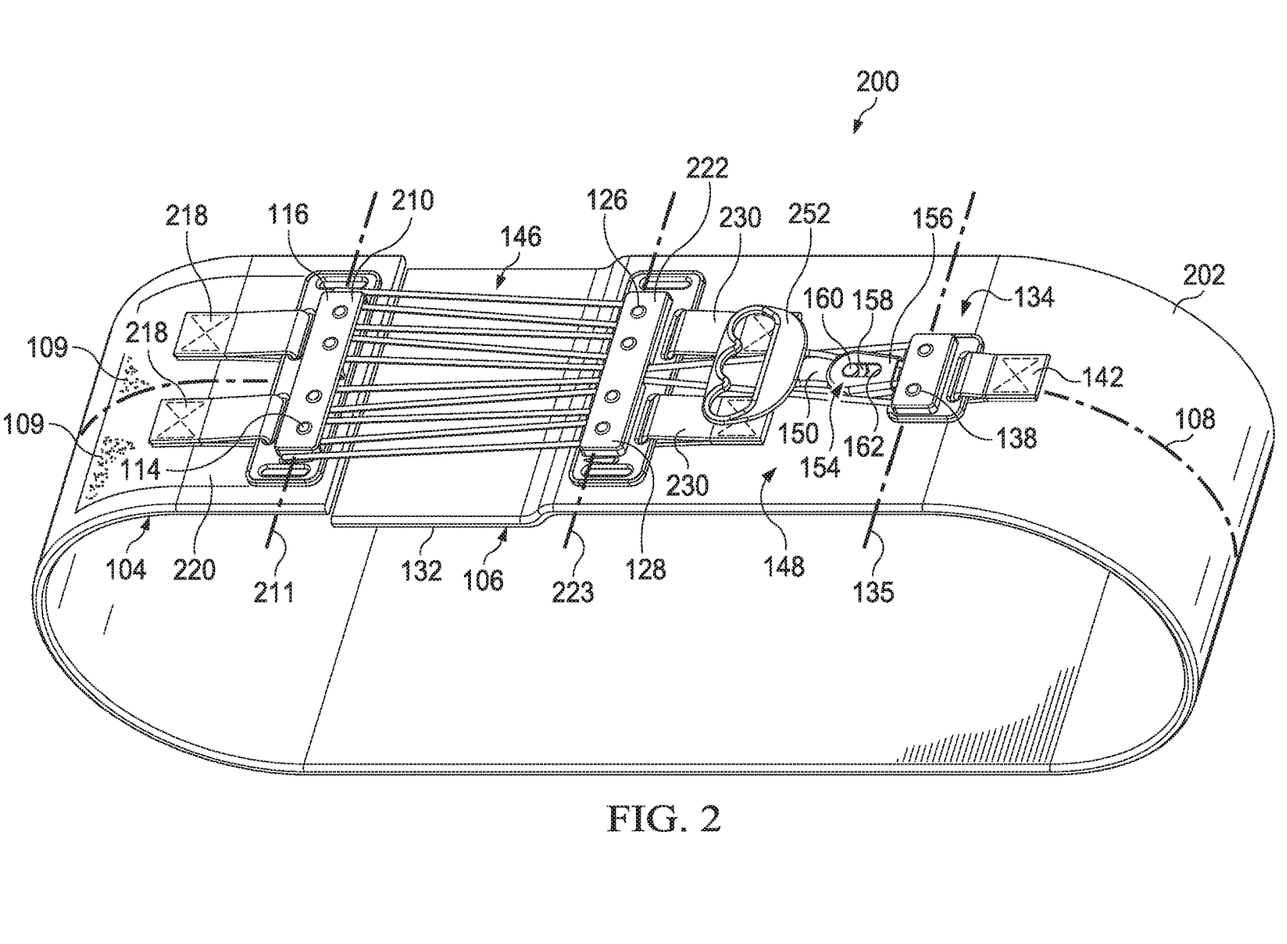
FIG. 2 shows a perspective view of a compression belt for selective temporary abdominal compression in accordance with another aspect.

Referring now to FIG. 2, there is illustrated a perspective view of a compression belt for selective temporary compression of a patient's abdomen, ribs, pelvis or other body portion in accordance with another aspect. The compression belt 200 will be described in greater detail below following the description of the first aspect.

Figure 3A:
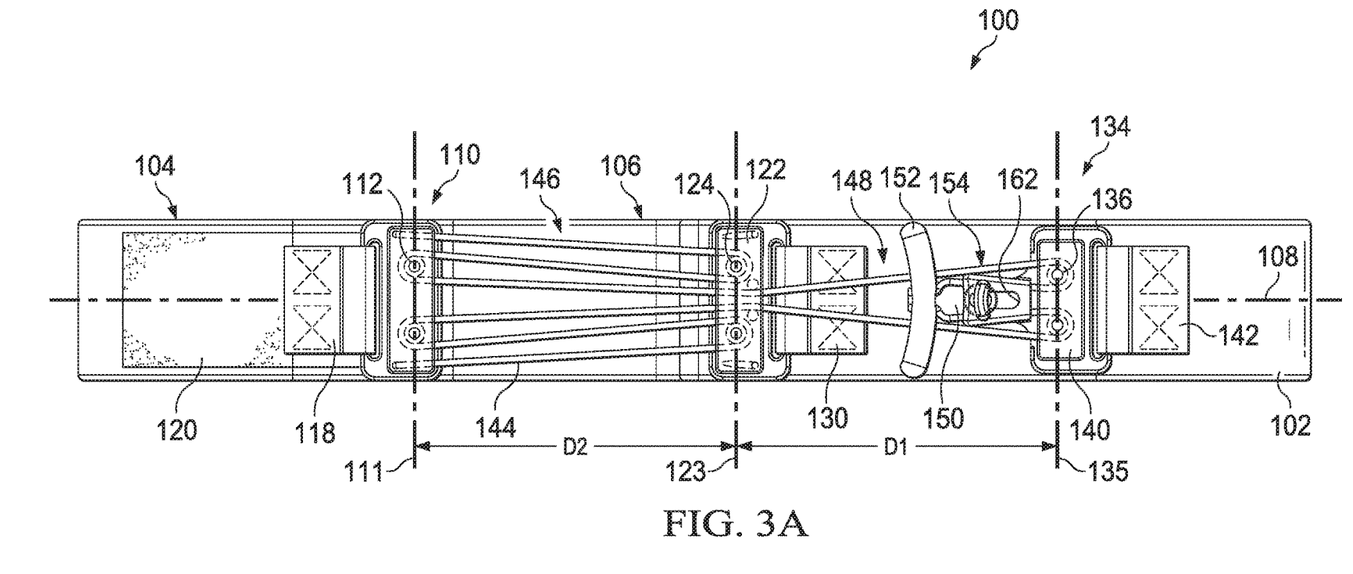
FIGS. 3A and 3B are, respectively, a top view and a side view of the compression belt of FIG. 1.
Figure 3B:
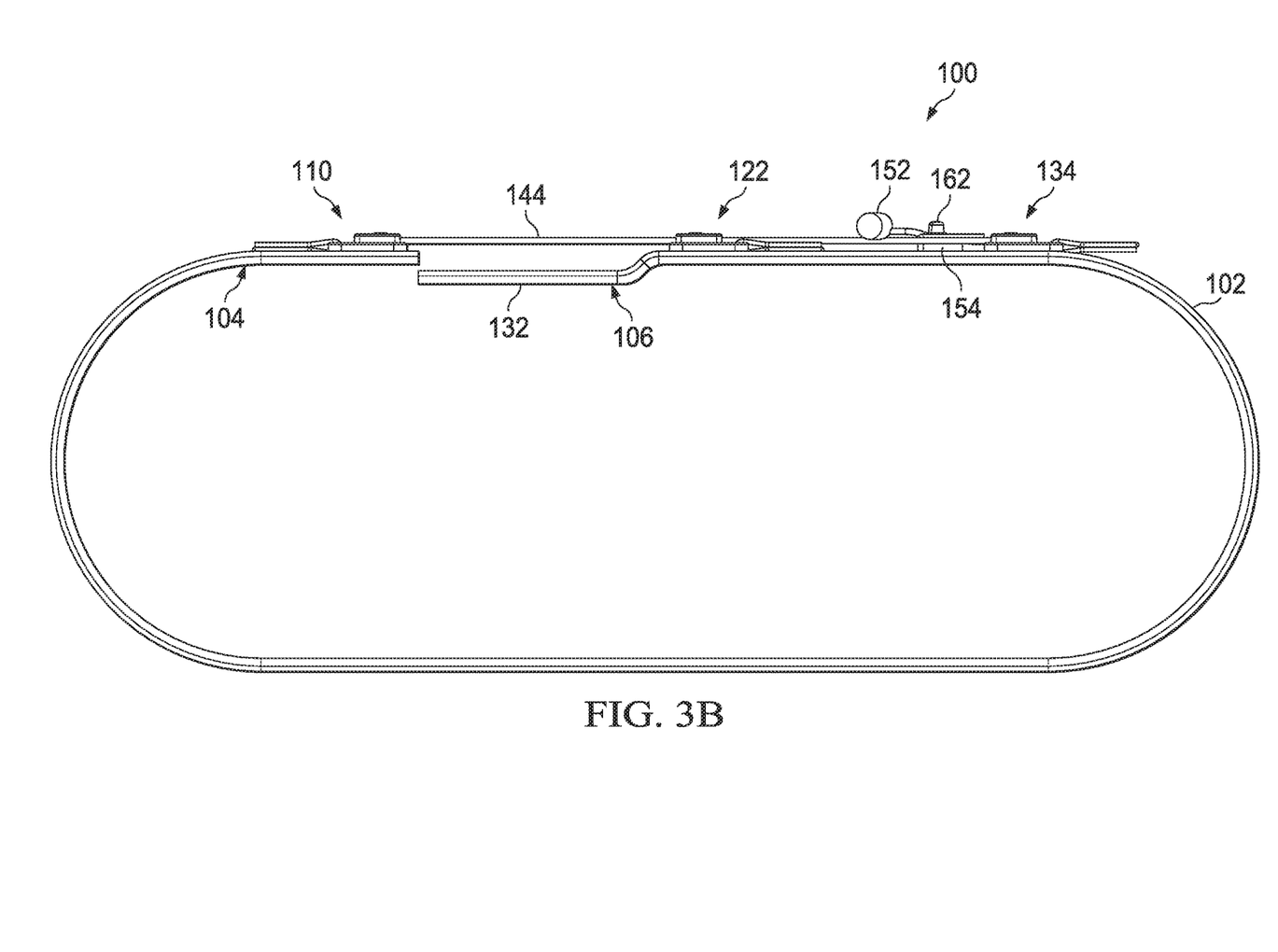

Referring again to FIG. 1, and now also to FIGS. 3A and 3B, a top view and side view of the compression belt 100 are shown to provide further details. A first pulley bank 110 is affixed to be first end portion 104. The first pulley bank 110 includes at least two pulleys 112 (see FIG. 3A) rotatably mounted on axles 114 within a housing 116. In the illustrated embodiment, the pulleys 112 of the first pulley bank 110 are arranged along a line 111 perpendicular to the centerline 108 of the belt body 102. In other embodiments, the pulleys 112 of the first pulley bank 110 may be arranged differently.

The first pulley bank 110 may be permanently affixed to the first end portion 104 of the belt body 102 in some embodiments, and releasably (i.e., removably or repositionably) affixed to the belt body in other embodiments. In the illustrated embodiment, the first pulley bank 110 is releasably affixed to the first end portion 104 by a flexible anchor strap 118 that is connected through a slot formed in the pulley housing 116. A quantity of hook-type fastening material is provided on the underside of the flexible anchor strap 118, and this hook-type material is used to engage loop-type fastening material provided in a fastening area 120 disposed on the first end portion 104. In this way, the compression belt 100 can be adjusted to size by choosing exactly where the flexible anchor strap 118 is attached within the fastening area 120. It is preferred to use loop-type fastening material on the surface of the belt body 102, since it has a softer feel than hook-type fastening material; however, the positions of the hook-type and loop-type fastening materials may be interchanged in other embodiments. In still other embodiments, other types of releasable fastening materials or devices may be used for releasably connecting the first pulley bank 110 to the belt body. In alternative embodiments, in which the first pulley bank 110 is permanently affixed to the first end portion 104, the flexible anchor strap 118 may be stitched, glued, riveted or otherwise connected to the belt body 102. In still other alternative embodiments, the pulley bank housing 116 may be stitched, glued or otherwise permanently attached directly to the belt body 102 without the use of the flexible anchor strap 118.

Referring still to FIGS. 1, 3A and 3B, the compression belt 100 further includes a second pulley bank 122 affixed to the second end portion 106. The second pulley bank 122 includes at least two pulleys 124 (see FIG. 3A) rotatably mounted on axles 126 within a housing 128. In the illustrated embodiment, the pulleys 124 of the second pulley bank 122 are arranged along a line 123 perpendicular to the centerline 108 of the belt body 102. In other embodiments, the pulleys 124 of the second pulley bank 122 may be arranged differently.

Similar to the first pulley bank 110, the second pulley bank 122 may be permanently affixed to the second end portion 106 of the belt body 102 in some embodiments, and releasably affixed to the belt body in other embodiments. However, in the illustrated embodiment, the second pulley bank 122 is permanently affixed to the second end portion 106 by a flexible anchor strap 130 that is connected through a slot formed in the pulley housing 128. The flexible anchor strap 130 is stitched to the belt body 102 in this embodiment, however in other embodiments gluing or other permanent affixing methods may be used. In alternative embodiments, the second pulley bank may be releasably fixed to the second end portion 106 as previously discussed in connection with the first pulley bank 110.

It will be appreciated that, while the second pulley bank 122 is affixed to the second end portion 106, the second pulley bank is not necessarily affixed at the extreme distal end of the belt body 102. In some embodiments, such as the one illustrated in FIG. 1, the second end portion 106 may include a free end section 132 at its extreme distal end. The free end section 132 may be tucked under the first end portion 104 when the belt body is positioned around the patient's body so that the first end portion "rides" on top of the free end section to reduce "pinching" or "bunching" when the compression belt is activated.

Referring still further to FIGS. 1, 3A and 3B, the compression belt 100 further includes a third pulley bank 134 affixed to the belt body 102 at a fixed distance, D1, from the second pulley bank 122. In some embodiments, the distance D1 may be about 6.0 inches. The third pulley bank 134 includes at least two pulleys 136 (see FIG. 3A) rotatably mounted on axles 138 within a housing 140. In the illustrated embodiment, the pulleys 136 of the third pulley bank 134 are arranged along a line 135 perpendicular to the centerline 108 of the belt body 102. In other embodiments, the pulleys 136 of the third pulley bank 134 may be arranged differently. As with the first two pulley banks, the third pulley bank 134 may be permanently affixed to the belt body 102 in some embodiments, and releasably affixed to the belt body in other embodiments. In the illustrated embodiment, the third pulley bank 134 is permanently affixed to the belt body 102 by a flexible anchor strap 142 that is connected through a slot formed in the pulley housing 140. The flexible anchor strap 142 is stitched to the belt body 102 in this embodiment, however in other embodiments gluing or other permanent affixing methods may be used. In alternative embodiments, the third pulley bank may be releasably fixed to the belt body 102, as previously discussed in connection with the first pulley bank 110 and the second pulley bank 122.

A flexible cord 144 interconnects the first, second and third pulley banks 110, 122, 134, the flexible cord having a first cord portion 146 extending between the pulleys 112, 124 of the first and second pulley banks 110, 122 in alternation. A second cord portion 148 is connected to the first cord portion 146 and extends between the pulleys 112, 136 of the first and third pulley banks 110, 134. A third cord portion 150 is connected at a first end to the second cord portion 148, and extends away from the third pulley bank 136.

The interconnection of the various portions 146, 148 and 150 of the flexible cord 144 through the respective pulleys 112, 124 and 136 of the three pulley banks 110, 122 and 134 creates a mechanical advantage mechanism substantially similar to a block and tackle. A handle 152 is connected to the second end of the third cord portion 150. Withdrawing the third cord portion 150 from the third pulley bank 134 by pulling the handle 152 away from the third pulley bank causes a shortening of the first cord portion 146 (i.e., the cord portion interconnected between the first pulley bank 110 and the second pulley bank 122) such that the distance D2 (see FIG. 3A) between the first and second pulley banks is reduced. This causes the belt body 102 to contract around the patient's body, applying circumferential compression to the portion of the patient's body underneath the compression belt 100. In other words, when the patient or technician pulls out on the handle 152 the flexible cord 144 runs through the block and tackle formed by the first second and third pulley banks 110, 122 and 134, and tightens the compression belt by moving the first and second pulley banks 110, 122 closer together (i.e., distance D2 is reduced). However, the distance D1 between the second and third pulley banks 122, 134 does not change when the handle 152 is pulled. In the illustrated embodiment, the handle 152 is an elongated, slightly curved cylinder forming a "T-shape" across the end of the third cord portion 150, and which is easy to grasp with one hand. In other embodiments, the handle 152 may have other shapes including, but not limited to, a D-ring style pull ring (see FIG. 2), with or without finger grooves, a ball, a ring or a heart-shaped pendant.

In preferred embodiments, the compression belt 100 further includes a selectively releasable one-way cord lock mechanism 154 connected to the belt body 102. The cord lock mechanism 154 includes a frame 156 defining a cord passage through which the third cord portion 150 is routed after leaving the third pulley bank 134. The cord lock mechanism 154 further includes a locking member 158 mounted in the frame 156 and movable between a locked position and a released position. A release member 160 is connected to the locking member 158 for moving the locking member between the locked position and a released position. Preferably, the release member 160 projects upwards from the cord lock mechanism 154 so that it is easily located by touch alone (i.e., without the patient or technician needing to see it).

In the illustrated embodiment of FIGS. 1, 3A and 3B, the cord lock mechanism 154 is connected directly to the housing 140 of the third pulley bank 134 such that the third cord portion 150 passes directly from the third pulley bank into the cord passage of the frame 156. In other embodiments, the cord lock mechanism 154 may be mounted directly to the belt body 102 or to another component of the belt 100. Further in the illustrated embodiment, the locking member 158 of the cord lock mechanism 154 comprises a toothed wheel which is mounted in a wedge-shaped slot 162 formed in the frame 156. The toothed wheel 158 can move laterally in the slot 162 to wedge the flexible cord 144 against the frame 156 in the locked position and to release the flexible cord so it can pass through the frame when in the unlocked position. Further still in the illustrated embodiment, the release member 160 includes a curved release handle 164 projecting from the upper surface of the frame 156. The curved release handle 164 assists the patient or technician in locating and activating the release member 160 in order to release the compression of the belt 100.

As it passes through the frame 156 of the locking mechanism 154, the third cord portion 150 is routed against the locking member 158 so as to bias the locking member toward the locked position. In the absence of external forces (such as activation of the release member 160), the biasing of the locking member 158 by the third cord portion 150 maintains the locking member in the locked position. The locking member 158, when in either of the locked position or the released position, allows withdrawal (i.e., pulling out) of the third cord portion 150 from the third pulley bank 134 to tighten the compression belt 100 and compress the selected portion of the patient's body. However, the locking member 158, when in the locked position, prevents the third cord portion 150 from retracting into the third pulley bank 134, thereby maintaining compression of the selected portion of the patient's body even if the patient or technician stops pulling on the handle 152. Thus, compression is maintained with "no hands required", i.e., in case the patient needs both hand for holding a walker, etc. or the technician is busy with other tasks. The locking member, 158, when in the released position, allows the third cord portion 150 to retract into the third pulley bank 134 to discontinue compression of the selected portion of the patient's body. Thus, by simply pulling the handle 152 with one hand, the patient or technician can selectively produce circumferential compression of the selected body portion by the belt 100, and the circumferential compression is maintained even if the patient or technician quits pulling on the handle. Subsequently, by pushing the release member 160 (or release handle 164) to the released position, the patient or technician can release any compression held by the belt 100.

Figure 4:
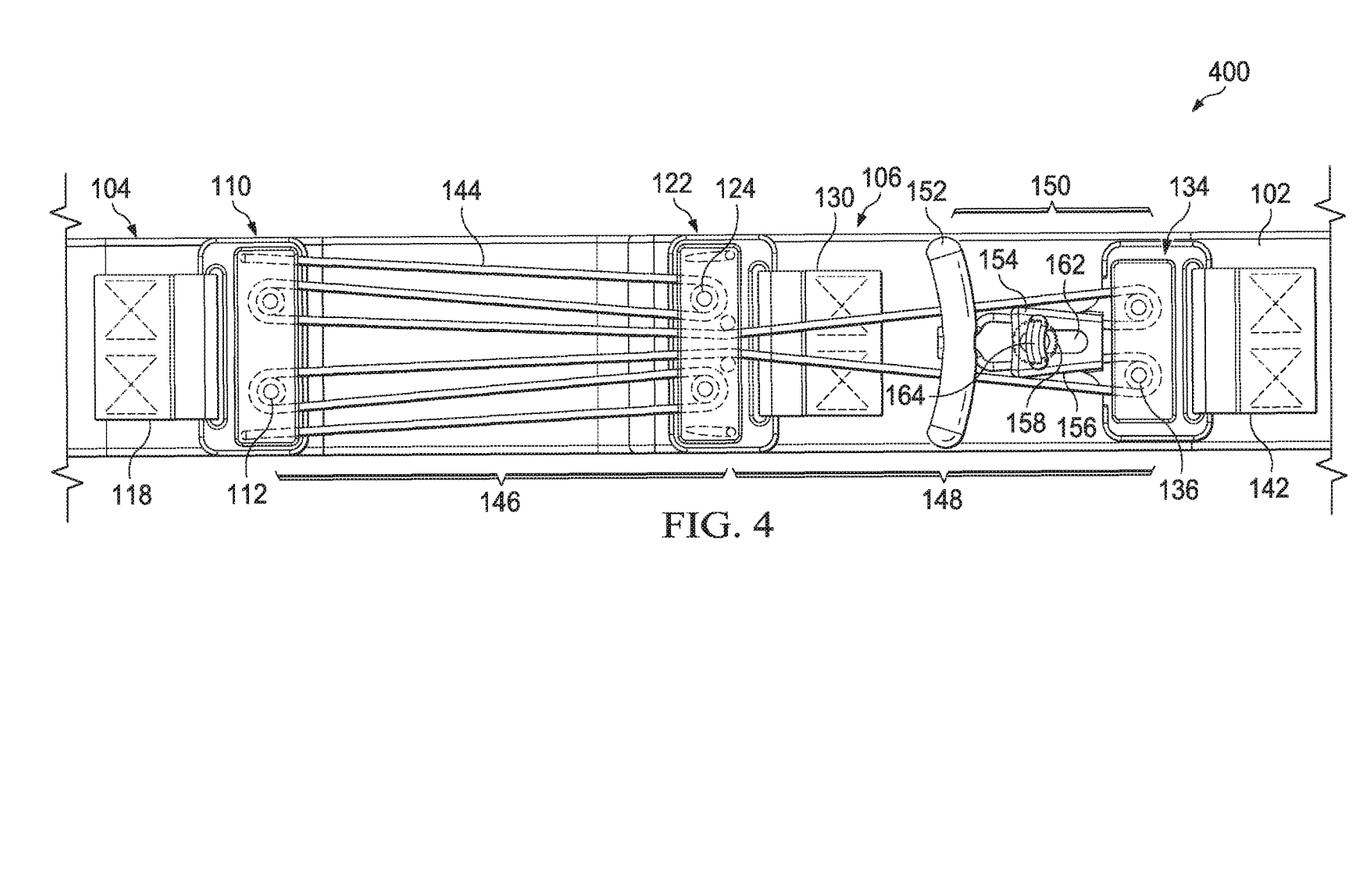
FIG. 4 is an enlarged partial top view of a compression belt similar to the compression belt of FIG. 1, in accordance with another embodiment.

Referring now to FIG. 4, there is illustrated an enlarged partial top view of a compression belt 400 similar to the compression belt 100 of FIG. 1, in accordance with another embodiment. The compression belt 400 is substantially similar in most respects to the belt 100 previously described, and therefore common reference numbers are used for similar elements.

Referring now again to FIG. 2, the compression belt 200 is substantially similar in many respects to the belt 100 previously described such a common reference numbers are used for similar elements. However, some aspects of compression belt 200 are changed to accommodate the different application. For example, in a preferred embodiment of the compression belt 200, the belt body 202 may have an overall width (measured perpendicular to the centerline 108) of about 5.0 inches and a length (measured along the centerline) of about 60 inches.

Figure 5A:
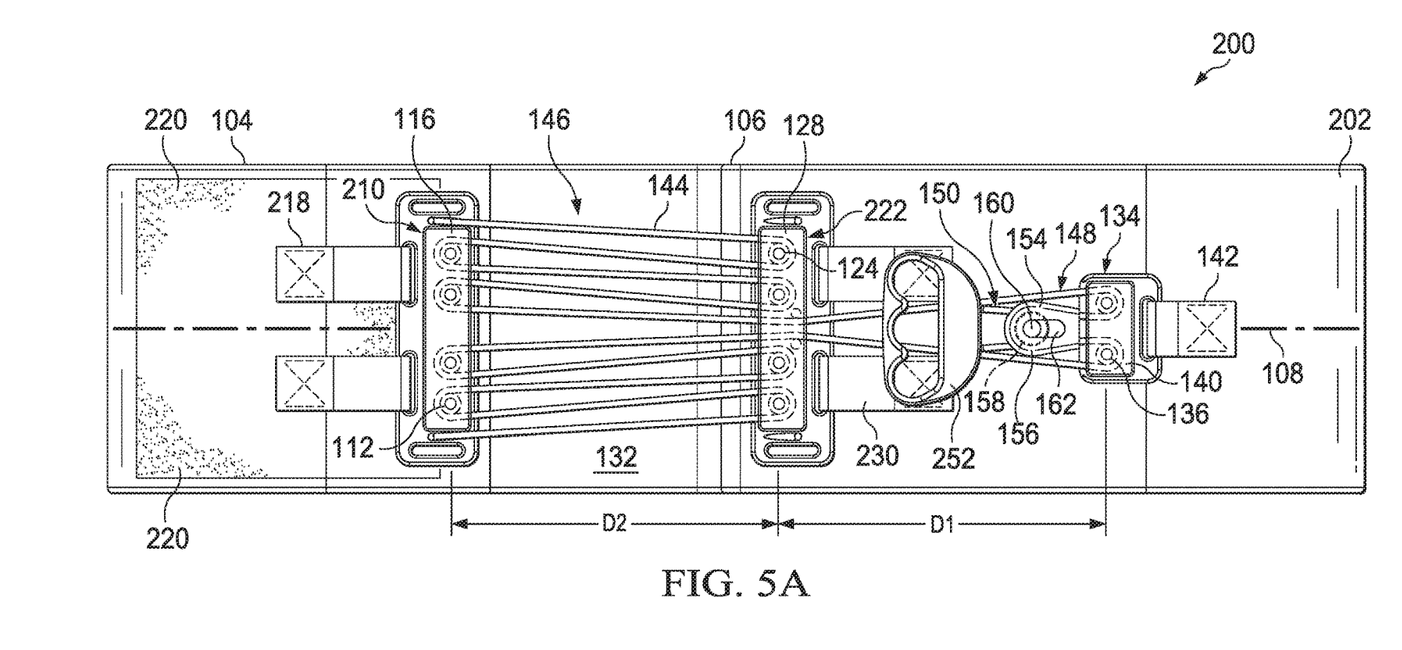
FIGS. 5A and 5B are, respectively, a top view and a side view of the compression belt of FIG. 2.
Figure 5B:
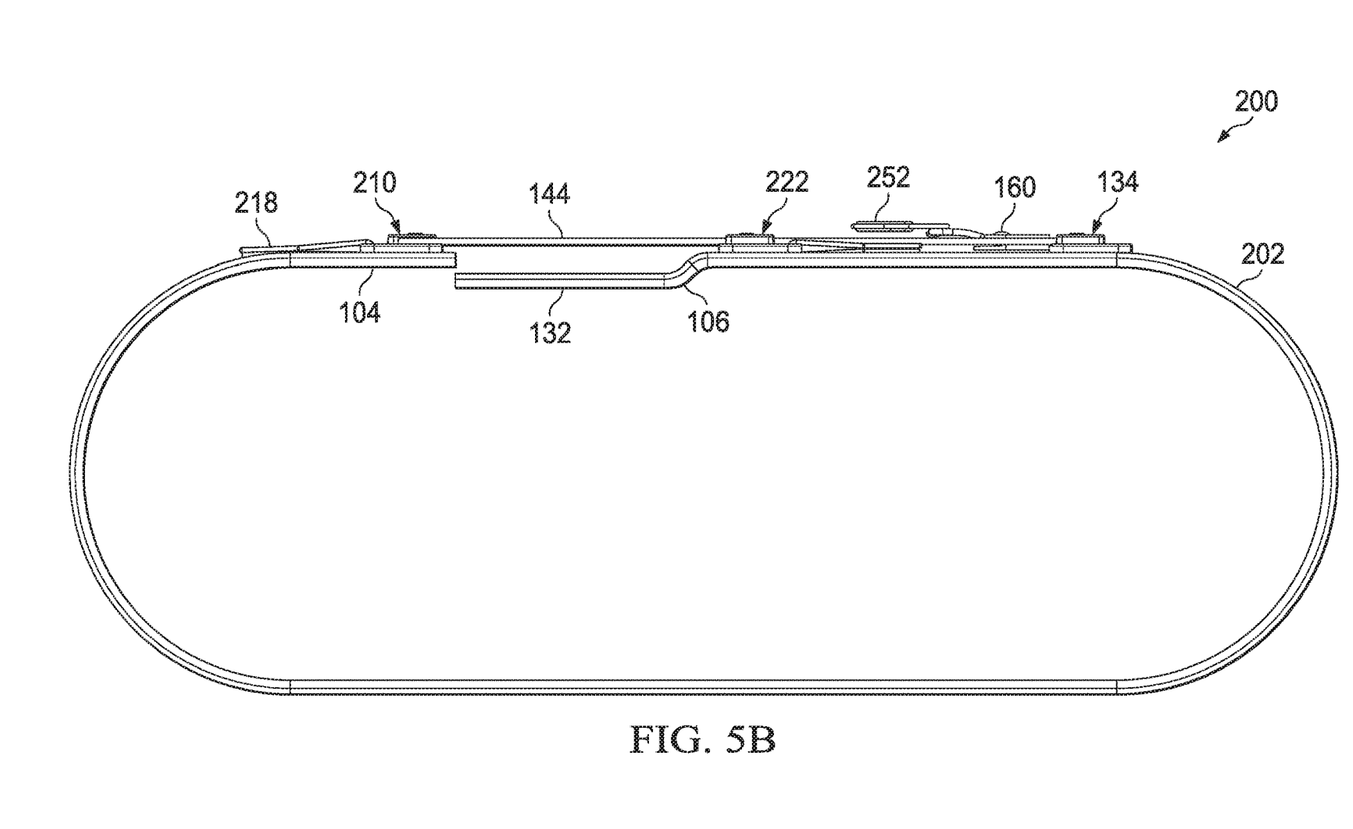

Referring still to FIG. 2, and also to FIGS. 5A and 5B, a top view and side view of the compression belt 200 are shown to provide further details. In particular, in compression belt 200, the first pulley bank 210 includes four pulleys 112 (see FIG. 5A) mounted on axles 114 within a housing 116. In the illustrated embodiment, the pulleys 112 of the first pulley bank 210 are arranged along a line 211 perpendicular to the centerline 108 of the belt body 202, however, in other embodiments, the pulleys 112 of the first pulley bank 210 may be arranged differently. Similarly, a compression belt 200 the second pulley bank 222 also includes four pulleys 124 (see FIG. 5A) mounted on axles 126 within a housing 128. In the illustrated embodiment, the pulleys 124 of the second pulley bank 222 are arranged along a line 223 perpendicular to the centerline of the belt body 202, however, in other embodiments, the pulleys 124 of the second pulley bank may be arranged differently. The third pulley bank 134 of the compression belt 200 may contain only two pulleys 136 as in the compression belt 100. The four-pulley pulley banks 210 and 222 interconnected by flexible cord 144 and also connected to the two-pulley pulley bank 134 results in a block-and-tackle mechanism for the compression belt 200 with a mechanical advantage of about 5:1, which is greater than the 3:1 mechanical advantage block-and-tackle mechanism of the compression belt 100.

It will further be appreciated that the pulley banks 210 and 222 are affixed to the belt body 202 using dual flexible anchor straps 218 and 230, respectively. In the illustrated embodiment of FIGS. 2, 5A and 5B, the flexible anchor straps 218 are releasably affixed to a fastening area 220 disposed on the first end portion 104 and the flexible anchor straps 230 are permanently affixed to the second free end portion 106. In addition, in this embodiment, the flexible anchor strap 142 on the third pulley bank 134 is permanently attached to the belt body 202. In other embodiments, the various anchor straps 218, 230, 142 may be attached or affixed in alternative manners as described in connection with compression belt 100.

In the illustrated embodiment of compression belt 200, a handle 252 having a D-ring style with finger grips is provided. The one way cord release mechanism 154 has a different external configuration, but functions in the same manner as the cord release mechanism previously described.

Figure 6:
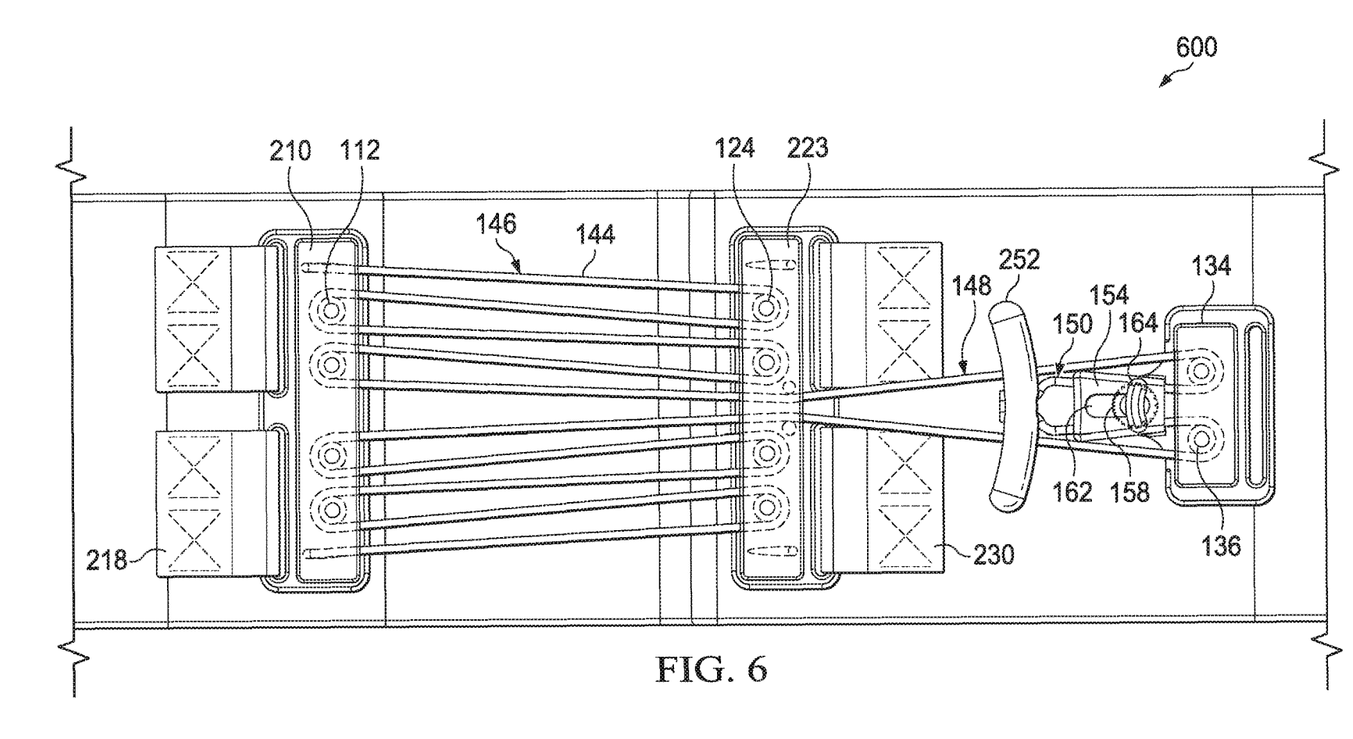
FIG. 6 is an enlarged partial top view of a compression belt similar to the compression belt of FIG. 2, in accordance with another embodiment.

Referring now to FIG. 6, there is illustrated an enlarged partial top view of a compression belt 600 similar to the compression belt 200 of FIGS. 2, 5A and 5B, in accordance with another embodiment. The compression belt 600 is substantially similar in most respects to the belt 200 previously described, and therefore common reference numbers are used for similar elements. Some of the changes include a new configuration for the pull handle 252, for the release handle 164 and for the configuration of the various pulley banks 210, 222 and 134.

Although the preferred embodiment has been described in detail, it should be understood that various changes, substitutions and alterations can be made therein without departing from the spirit and scope of the invention as defined by the appended claims.

It will be appreciated by those skilled in the art having the benefit of this disclosure that new and improved compression belts for selective chest compression following thoracic and cardiothoracic surgery, for selective abdominal compression following abdominal surgery, for stabilization of rib fractures and for emergency stabilization of pelvic fractures are described. It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. A compression belt for encircling a selected portion of a patient's body and providing temporary circumferential compression of the selected portion of the patient's body, the compression belt comprising:

an elongated belt body having a continuous length with opposing first and second free end portions and defining a centerline extending therebetween, the belt body adapted to be wrapped circumferentially around the selected portion of the patient's body;

a first pulley bank affixed to the first end portion, the first pulley bank including at least two pulleys arranged perpendicular to the centerline of the belt body;

a second pulley bank affixed to the second end portion, the second pulley bank including at least two pulleys arranged perpendicular to the centerline of the belt body;

a third pulley bank affixed to the belt body at a fixed distance from the second pulley bank, the third pulley bank including at least two pulleys arranged perpendicular to the centerline of the belt body;

a flexible cord interconnecting the first, second and third pulley banks, the cord having
- a first cord portion extending between the pulleys of the first and second pulley banks in alternation,
- a second cord portion connected to the first cord portion and extending between the pulleys of the first and third pulley banks, and
- a third cord portion connected to the second cord portion and extending away from the third pulley bank;

a handle connected to the third cord portion, whereby withdrawing the third cord portion from the third pulley bank by pulling the handle away from the third pulley bank causes a shortening of the first cord portion such that the first and second pulley banks move closer together along with the first and second free end portions to which the respective pulley banks are affixed, thereby tightening the belt body around the selected portion of the patient's body and compressing the selected portion of the patient's body; and a selectively releasable one-way cord lock mechanism connected to the belt body, the cord lock mechanism including a frame defining a cord passage through which the third cord portion is routed after leaving the third pulley bank, a locking member mounted in the frame and movable between a locked position and a released position, the third cord portion being routed against the locking member so as to bias the locking member toward the locked position, and a release member connected to the locking member for moving the locking member between the locked position and the released position;

whereby the locking member,
- when in either the locked position or the released position, allows withdrawal of the third cord portion from the third pulley bank to compress the selected portion of the patient's body,
- when in the locked position, prevents the third cord portion from retracting into the third pulley bank to maintain compression of the selected portion of the patient's body, and
- when in the released position, allows the third cord portion to retract into the third pulley bank to discontinue compression of the selected portion of the patient's body.

2. A compression belt in accordance with claim 1, wherein the compression belt is adapted for encircling a chest area of a post-thoracic or post-cardiothoracic surgery patient.

3. A compression belt in accordance with claim 1, wherein the compression belt is adapted for encircling an abdominal area of a post-abdominal surgery patient.

4. A compression belt in accordance with claim 1, wherein the first pulley bank is permanently affixed to the first end portion.

5. A compression belt in accordance with claim 1, wherein the first pulley bank is releasably affixed to the first end portion.

6. A compression belt in accordance with claim 5, further comprising:
   loop-type fastening material provided in a fastening area disposed on the first end portion; and
   a quantity of hook-type fastening material connected to the first pulley bank; and
   wherein the first pulley bank is releasably affixed to the first end portion by engaging the loop-type fastening material with the quantity of hook-type fastening material.

7. A compression belt in accordance with claim 6, further comprising:
   a flexible anchor strap connected to the first pulley bank; and
   wherein the quantity of hook-type fastening material is provided on an underside of the flexible anchor strap.

* * * * *